US00PP31629P3

(12) United States Plant Patent
van Langen

(10) Patent No.: US PP31,629 P3
(45) Date of Patent: Mar. 31, 2020

(54) ***PACHYVERIA* PLANT NAMED 'TSAECH1708'**

(50) Latin Name: ***Pachyphytum caerulea* x *Echeveria lilacina*, x *Pachyveria* spp.**
Varietal Denomination: TSAECH1708

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 16/350,122

(22) Filed: Sep. 27, 2018

(65) Prior Publication Data

US 2019/0098822 P1 Mar. 28, 2019

(30) Foreign Application Priority Data

Sep. 27, 2017 (QZ) ..... PBR 2017/2391

(51) Int. Cl.
*A01H 5/12* (2018.01)
*A01H 6/32* (2018.01)
*A01H 6/00* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373, 263.1
CPC ... A01H 5/12; A01H 5/00; A01H 5/02; A01H 6/32
See application file for complete search history.

(56) References Cited

PUBLICATIONS

Community Plant Variety Office Plant Breeder's Right Application 2017/2391 16 pp. (Year: 2017).*
Upov Pluto Plant Variety Database Jul. 13, 2019, retrieved on Jul. 15, 2019, retrieved from the Internet at https://www3.wipo.int/pluto/user/en/index.jsp, one page. (Year: 2019).*

* cited by examiner

*Primary Examiner* — June Hwu
(74) *Attorney, Agent, or Firm* — Samuel R. McCoy, Jr.

(57) ABSTRACT

A new and distinct *Pachyveria* plant named 'TSAECH1708' which is characterized by small, broad obovate foliage arranged in a basal rosette, foliage which is very upright at the center of the rosette and becoming progressively more relaxed towards the outer whorls of the rosette, glaucous greyed-green foliage with a pinkish hue towards the distal end, as well as the stability of these characteristics from generation to generation.

3 Drawing Sheets

Latin name of the genus and species: The Latin name of the genus and species of the novel variety disclosed herein is *Pachyphytum caeruleas* x *Echeveria lilacina* which is also known by the nothogenus, x *Pachyveria* spp. (hereinafter referenced as, "*Pachyveria*").

Variety denomination: The inventive variety of *Pachyveria* hybrid disclosed herein has been given the variety denomination 'TSAECH1708'.

CROSS REFERENCE TO RELATED APPLICATIONS

This application claims priority to the Community Plant Variety Rights application number 2017/2391, filed Sep. 27, 2017, which is herein incorporated by reference.

BACKGROUND OF THE INVENTION

Parentage: 'TSAECH1708' is an intergeneric hybrid seedling selection resulting from the controlled pollination of an unnamed *Pachyphytum caerulia* plant (not patented), the seed parent, with an unnamed *Echeveria lilacina* plant (not patented), the pollen parent. The crossing was made by the inventor in the spring of 2015 at a commercial greenhouse in Heerhugowaard, the Netherlands. In the spring of 2016, one seedling was observed which exhibited unique growth and foliage characteristics. The seedling was isolated for further evaluation in order to confirm the distinctness and stability of the characteristics first observed. Upon confirmation of distinctness and stability, 'TSAECH1708' was selected for commercialization in the autumn of 2016.

Asexual Reproduction: Asexual reproduction of the new cultivar 'TSAECH1708', by way of rooting leaf cuttings, was first initiated in the spring of 2017 at the inventor's commercial greenhouse in Heerhugowaard, the Netherlands. Through four subsequent generations, the unique features of this cultivar have proven to be stable and true to type.

SUMMARY OF THE INVENTION

The cultivar 'TSAECH1708' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1708'. These characteristics in combination distinguish 'TSAECH1708' as a new and distinct *Pachyveria* cultivar:

1. 'TSAECH1708' exhibits small, succulent foliage arranged in a basal rosette; and 2. 'TSAECH1708' exhibits broad obovate foliage which is curved upwards; and
3. 'TSAECH1708' exhibits foliage which is very upright at the center of the rosette, becoming progressively more relaxed towards the outer whorls of the rosette; and
4. 'TSAECH1708' exhibits glaucous greyed-green foliage with a light pinkish hue towards the distal end.

BOTANICAL DESCRIPTION OF THE PLANT

Figure 1:
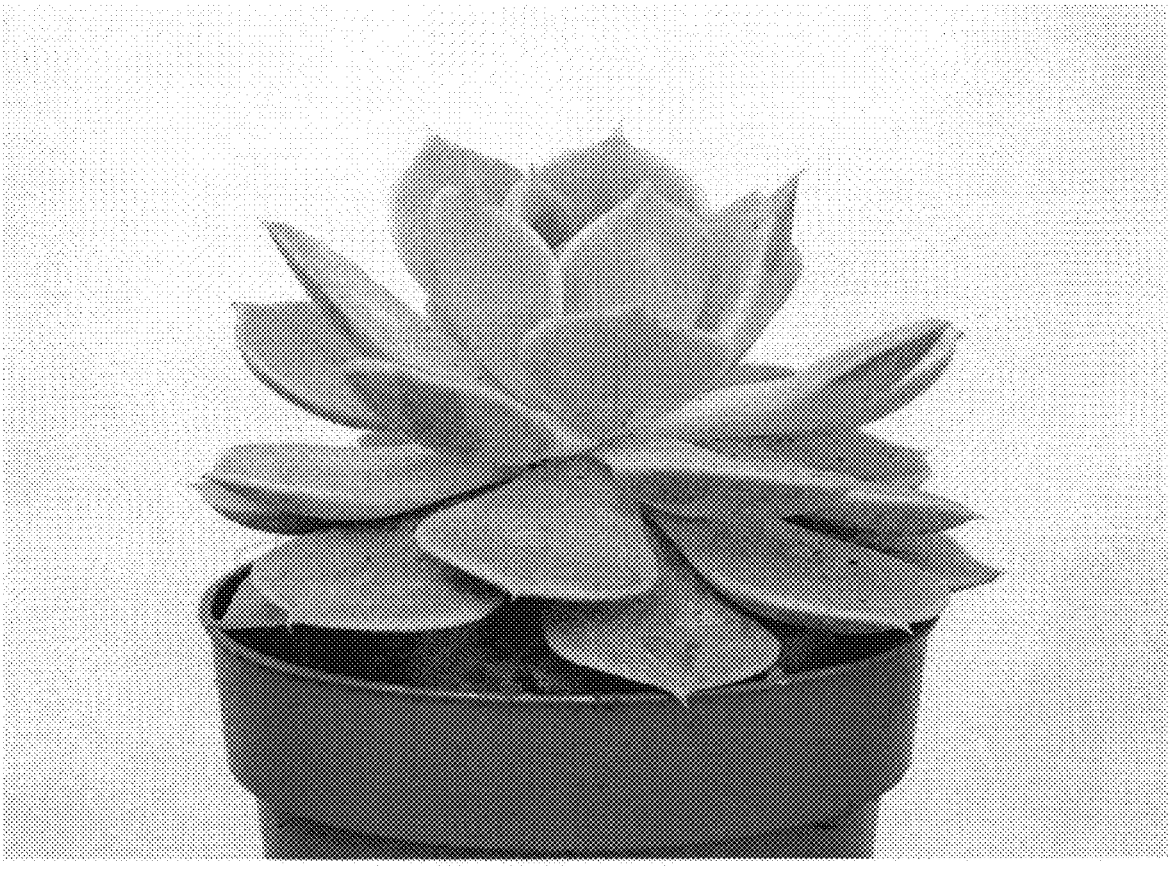
FIG. 1 illustrates, as nearly true as it is reasonably possible to make the same in color photographs of this type, an exemplary plant of 'TSAECH1708' grown in a commercial greenhouse in Heerhugowaard, the Netherlands. This plant is approximately 6 months old, shown planted in an 8.5 cm container.
Figure 2:
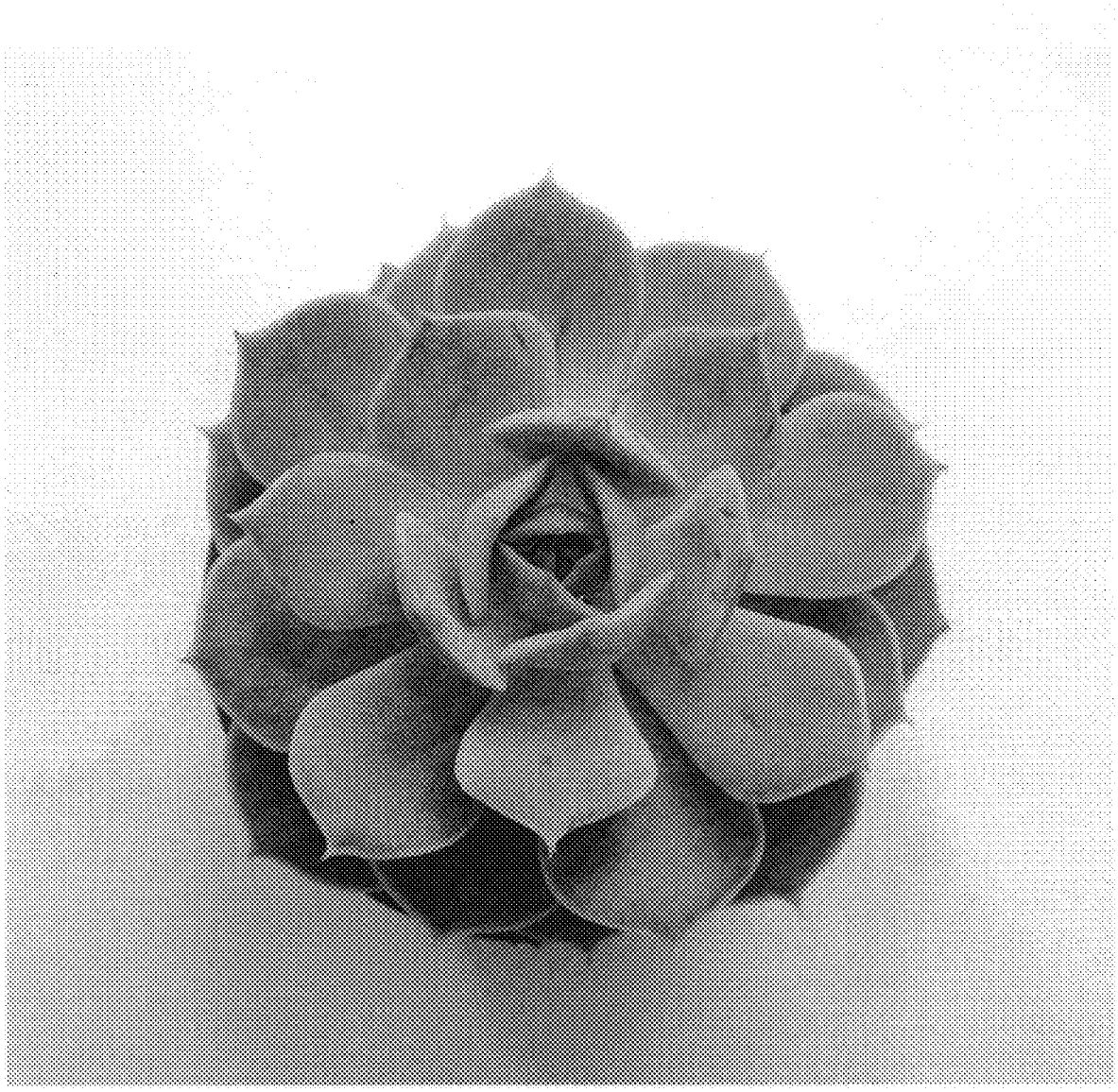
FIG. 2 illustrates, as nearly true as it is reasonably possible to make the same in color photographs of this type, the typical foliage arrangement of 'TSAECH1708'.
Figure 3:
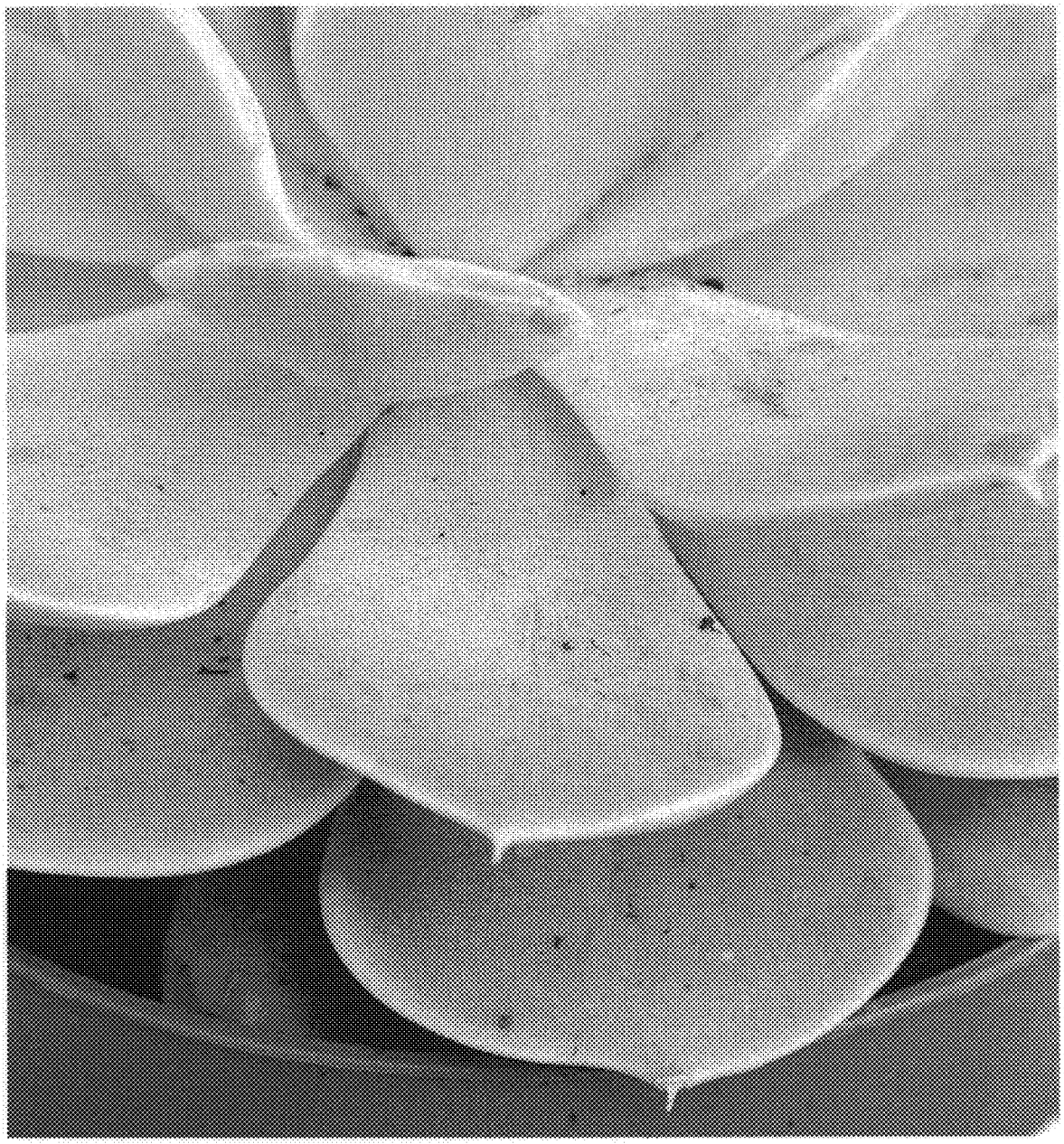
FIG. 3 illustrates, as nearly true as it is reasonably possible to make the same in color photographs of this type, the typical mature foliage of 'TSAECH1708'.

The following observations and measurements made in August of 2018 describe averages from a sample set of six specimens of 6 months old 'TSAECH1708' plants grown in 8.5 cm nursery containers at commercial greenhouse in Heerhugowaard, the Netherlands. Plants were produced using conventional greenhouse production protocols for *Echeveria* and *Pachyphytum* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1708' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1708' and comparisons with the parent plants and closest known comparator are provided below.

Plant description:

*Growth habit.*—Succulent perennial with foliage growing in a non-branched basal rosette.

*Plant shape.*—Flattened globular.

*Height from soil level to top of foliar plane.*—6.9 cm.

*Plant spread.*—Average of 9.7 cm.

*Growth rate.*—Low to moderate.

*Plant vigor.*—Moderate.

*Propagation.*—Type — Leaf cuttings. Time to initiate rooting — Approximately 21 days at 18 degrees Celsius. Crop time — Approximately 35 weeks to produce a marketable plant in an 11 cm container.

*Disease and pest resistance or susceptibility.*—Neither resistance nor susceptibility to typical *Echeveria* and *Pachyphytum* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Stems:

*Branching habit.*—Leaves in a non-branching basal rosettes; no main branches or lateral branches present.

Foliage:

*Arrangement.*—Rosette.

*Division.*—Simple.

*Attachment.*—Sessile.

*Quantity.*—Approximately 35 leaves per rosette.

*Shape.*—Broad obovate.

*Dimensions.*—4.4 cm long, 2.7 cm wide, and 0.7 cm thick, on average.

*Aspect.*—Very slightly concave and slightly to moderately curved upward.

*Attitude.*—Younger foliage near the center of the rosette is very upright; foliage becoming progressively more relaxed towards the outer whorl of the rosette.

*Apex.*—Broad acute to apiculate with the tip curled upward.

*Base.*—Cuneate.

*Margin.*—Entire; not undulated or lobed.

*Pubescence, texture and luster of the adaxial surface.*—Glabrous, smooth, and matte; moderately glaucous.

*Pubescence, texture and luster of the abaxial surface.*—Glabrous, smooth, and matte; moderately glaucous.

*Color.*—Juvenile foliage, adaxial surface — Greyed-green, nearest to RHS 191A, and fading lighter towards the base, nearest to RHS 192D; narrowly margined with a lighter shade of greyed-green, nearest to RHS 193A; the epicuticular glaucous wax covering the leaf surface is greyed-green, nearest to a mixture of 188A and 188B. Juvenile foliage, abaxial surface — Greyed-green, nearest to RHS 191B, and fading lighter towards the base, nearest to RHS 192D; narrowly margined with a lighter shade of greyed-green, nearest to RHS 193A; the epicuticular glaucous wax covering the leaf surface is greyed-green, nearest to a mixture of RHS 188A and 188B. Mature foliage, adaxial surface — Greyed-green, nearest to RHS 195A, and fading lighter towards the base, nearest to a mixture of RHS 194B and 194C; narrowly margined with a considerably darker shade of greyed-green, nearest to RHS 193A; the epicuticular glaucous wax covering the leaf surface is greyed-green, nearest to a mixture of RHS 188A and 188B. The combination of the darker greyed-green foliage and the lighter greyed-green glaucous wax creates the illusion of a pinkish hue which is not measurable and does not correspond to any color notation in the *The Royal Horticultural Society Colour Chart*. Mature foliage, abaxial surface — Greyed-green, nearest to in between RHS 194A and 195A, and fading lighter towards the base, nearest to RHS 194D; narrowly margined with a slightly darker shade of greyed-green, nearest to RHS 193A; the epicuticular glaucous wax covering the leaf surface is greyed-green, nearest to a mixture of RHS 188A and 188B. The combination of the darker greyed-green foliage and the lighter greyed-green glaucous wax creates the illusion of a pinkish hue which is not measurable and does not correspond to any color notation in the *The Royal Horticultural Society Colour Chart*.

*Venation.*—No venation is visible.

*Petiole.*—No petiole; leaves are sessile.

Inflorescence: No flowering has been observed to date.

COMPARISONS WITH THE PARENT PLANT AND CLOSEST KNOWN COMPARATOR

Plants of the new cultivar 'TSAECH1708' differ from the seed parent, an unnamed *Pachyphytum* sp. plant (not patented), in the following characteristics described in Table 1 below.

TABLE 1

| Characteristic | 'TSAECH1708' | Seed parent. |
|---|---|---|
| Growth habit. | Flattened globular shape, with a more symmetrical rosette of foliage. | Globular shape, with foliage in a more irregular rosette. |
| Foliage cross-section. | Flattened. | Rounded. |
| General coloration of the mature foliage, | Greyed-green with a pinkish hue. | Appearing as a light blue-grey, and suffused with a mixture of lilac and pink. |

Plants of the new cultivar 'TSAECH1708' differ from the pollen parent, an unnamed *Echeveria lilacina* plant (not patented), in the following characteristics described in Table 2 below.

TABLE 2

| Characteristic | 'TSAECH1708' | Pollen parent |
|---|---|---|
| Leaf size. | Smaller than the pollen parent. | Larger than 'TSAECH1708'. |
| General coloration of the mature foliage. | Greyed-green with a pinkish hue. | Very light grey, nearly white, and suffused pink. |

COMPARISONS WITH THE CLOSEST KNOWN COMPARATOR

Plants of the new cultivar 'TSAECH1708' differ from the closest known commercial comparator, *Echeveria* sp. 'Lola' (not patented), in the following characteristics described in Table 3 below.

TABLE 3

| Characteristic | 'TSAECH1708' | Echeveria sp. 'Lola' |
|---|---|---|
| Plant size. | Smaller than 'Lola'. | Larger than 'TSAECH1708'. |
| Foliage size. | Smaller than 'Lola'. | Larger than 'TSAECH1708'. |
| General coloration of the foliage, | Greyed-green with a pinkish hue. | Light grey and suffused pink. |

That which is claimed is:

1. A new and distinct variety of *Pachyveria* hybrid plant named 'TSAECH1708', substantially as described and illustrated herein.

* * * * *